United States Patent
Mekouar et al.

(10) Patent No.: US 6,670,377 B1
(45) Date of Patent: Dec. 30, 2003

(54) QUINOLINE DERIVATIVES, HAVING IN PARTICULAR ANTIVIRAL PROPERTIES, PREPARATION AND BIOLOGICAL APPLICATIONS THEREOF

(75) Inventors: Khalid Mekouar, Paris (FR); Jean D'Angelo, Massy (FR); Didier Desmaele, Fresnes (FR); Jean-Francois Mouscadet, Paris (FR); Frèdèric Subra, Paris (FR); Christian Auclair, Paris (FR)

(73) Assignee: Centre National de la Recherche, Paris Cedex (FR)

( * ) Notice: Subject to any disclaimer, the term of this patent is extended or adjusted under 35 U.S.C. 154(b) by 0 days.

(21) Appl. No.: 09/402,858

(22) PCT Filed: Apr. 7, 1998

(86) PCT No.: PCT/FR98/00701
§ 371 (c)(1),
(2), (4) Date: Jan. 16, 2001

(87) PCT Pub. No.: WO98/45269
PCT Pub. Date: Oct. 15, 1998

(30) Foreign Application Priority Data

Apr. 8, 1997 (FR) ............................................. 97 04289

(51) Int. Cl.[7] ...................... A61K 31/47; C07D 215/16; C07D 215/20
(52) U.S. Cl. ...................... 514/314; 514/312; 546/153; 546/157
(58) Field of Search ................................. 546/153, 157; 514/312, 314

(56) References Cited

FOREIGN PATENT DOCUMENTS

| | | |
|---|---|---|
| DE | 3405 395 | 8/1984 |
| EP | 0 206 751 | 12/1986 |
| EP | 0 219 307 | 4/1987 |
| EP | 0256 180 | 2/1988 |
| EP | 0 286 089 | 10/1988 |
| EP | 0 318 093 | 5/1989 |
| EP | 0 643 045 | 3/1995 |
| EP | 0 725 063 | 8/1996 |
| WO | WO 94/27968 | 12/1994 |
| WO | WO 96/02506 | 2/1996 |
| WO | WO 96/04246 | 2/1996 |

OTHER PUBLICATIONS

Tsizin, CA 70:87516, abstract, 1967.*
Uchiyama, CA 127:65671, abstract, 1997.*
Kido, CA 27:307310, abstract, 1997.*
Mekouar, CA 129:290072, abstract, 1998.*
Mekouar, CA 129:148898, abstract, 1998.*
Tak., B.K., et al., "Influence of solvent interaction on the absorption spectra of some phenol betaines. II", Chemical Abstracts, vol. 77, No. 7, Aug. 14, 1972, p. 407, CA 47548 q.
Burke, Jr., T.R., et al., "Hydroxylated Aromatic Inhibitors of HIV–1 Integrase", *J. Med. Chem.*, vol. 38, 1995, pp. 4171–41798.
Phillips, J.P., et al., "Styryl Derivatives of 8–Quinolinol", *J. Am. Chem. Soc.*, vol. 24, 1959, pp. 1104–1106.

* cited by examiner

*Primary Examiner*—D. Margaret Seaman
(74) *Attorney, Agent, or Firm*—Foley & Lardner

(57) ABSTRACT

The invention concerns quinoline derivatives of formula (I) in which: $R_a$, $R_b$ and $R_c$, identical or different represent one or several substituents, themselves identical or different, in any position on the cycles, this or these substituents being selected among a —$(CH_2)_n$—Y or —CH=CH—Y group, in which Y is halogen, —OH, —OR, —COH, —COR, —COOH, COOR, —COH, —COR, —CONH$_2$, —CON($R_x$, $R_y$)—CH=NOH, —CO— —CH=NOH, —NH$_2$, —N($R_x$, $R_y$), —NO$_2$, —PO(OR)$_2$—SH$_2$, —SR, —SO$_2$R, —SO$_2$NHR, CN, or Z($R_c$) in which R is a C1–C8 alkyl, or aryl or a heterocyclic compound, $R_x$ and $R_y$, identical or different are C1–C5 alkyl, an aryl or heterocyclic compound and n is nil or a whole number between 1 and 5 $R_b$ can further represent a hydrogen, and when Y is —COOH or —COOR in $R_c$, Z, if it represents an aryl, comprises at least 3 substituents or the quinoline ring is trisubstituted; X is an ethylene double bond; a —$(CH_2)_n$— group in which n is a whole number between 1 and 5: or a —CH($R_d$—CH($R_e$) group, $R_d$ and $R_e$, identical or different, representing a hydrogen, a halogen, hydroxy or epoxy; or a —$(CH_2)_n$, —O—C—$(CH_2)_m$—, —$(CH_2)_n$, —C(O)—O—$(CH_2)_m$—, —$(CH_2)_n$, —O—$(CH_2)_m$—, $(CH_2)_n$, —N(Q)—$(CH_2)_m$—, or $(CH_2)_n$, —S(O)—$(CH_2)_m$—, group, in which n=1 to 8, m=0 to 8, t=0, 1 or 2, and Q=h, aryl or alkyl. The invention also concerns the pharmaceutically acceptable salts of these derivatives, the diastereoisomeric and the enantiomeric forms thereof. The invention is useful as medicines with HIV anti-integrase inhibiting effect.

12 Claims, No Drawings

QUINOLINE DERIVATIVES, HAVING IN PARTICULAR ANTIVIRAL PROPERTIES, PREPARATION AND BIOLOGICAL APPLICATIONS THEREOF

This application is a 371 of PCT/FR98/00701, filed Apr. 7, 1998.

A subject of the present invention is quinoline derivatives, in particular endowed with inhibitory properties of human immuno-deficiency virus integrase.

It also relates to a synthetic process for these derivatives and their biological uses.

The integration of the genomic DNA of HIV in the chromosomes of the infected cell is strictly necessary for the replication of the virus. The viral enzyme which catalyzes the integration of the viral DNA in the chromatin of the host is integrase. Consequently, an integrase inhibitor constitutes ipso facto a candidate for blocking infection by HIV, and possibly an effective therapeutic agent. Of the three viral enzymes which condition the replication of HIV, namely reverse transcriptase, protease and integrase, integrase is the last not to be targeted by any therapeutic agent. In the context of polytherapy, which currently seems to be only method of effectively combatting the rapid development of the virus, obtaining an integrase inhibitor is an essential objective.

Various groups across the world have developed integrase inhibitors, some of these molecules have submicromolar inhibitory activities in vitro, such as quercetagenin. Other compounds had promising activities such as phenyl ethyl esters of caffeic acid, cosalane, 5,8-dihydroxy-1,4-naphthoquinone, cucurmin, 1,10-phenanthroline, primaquine, chloroquine, certain derivatives of podophyllotoxin or also bis-gallic esters. However, the activites of these different products have only been reported in vitro and these products have not been shown to be active in vivo.

More recently, bis-caffeates of quinic acid have been described as active in vivo but depending on protocols involving bringing the drug into contact with the virus beforehand.

The work of inventors in this field has led them to study quinoline derivatives and to demonstrate anti-integrase properties in vitro as well as in vivo, these properties being accompanied by significant innocuity.

A subject of the invention is therefore to provide new quinoline derivatives capable in particular of inhibiting the integrase activity of HIV in vitro and in vivo.

It also relates to a synthetic process for these derivatives which can be easily implemented on an industrial scale.

A subject of the invention is also to exploit the anti-integrase properties of these derivatives for the development of medicaments.

The derivatives according to the invention are characterized in that they correspond to the general formula I Formula I

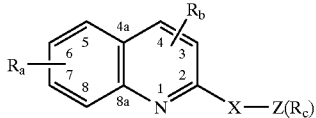

in which $R_a$, $R_b$ and $R_c$, identical or different from one another, represent one or more substituents, themselves identical or different, occupying any position on the rings, this or these substituents being chosen from a —$(CH_2)_n$—Y or —CH=CH—Y group, where Y represents a halogen atom, an —OH, —OR, —COH, —COR, —COOH, —COOR, —COH, —COR, —CONH$_2$, —CON($R_x$, $R_y$)—CH=NOH, —CO—CH=NOH, —NH$_2$, —N($R_x$, $R_y$), —NO$_2$, —PO(OR)$_2$—SH$_2$, —SR, —SO$_2$R, —SO$_2$NHR, CN, or Z($R_c$) radical, where R represents an alkyl radical with 1 to 8 carbon atoms, or an aryl or heterocyclic radical, $R_x$ and $R_y$, identical or different, represent an alkyl radical with 1 to 5 carbon atoms, Z represents an aryl or heterocyclic radical and n is zero or an integer between 1 and 5, $R_b$ moreover can represent a hydrogen atom, and when Y represents a —COOH or —COOR group in $R_c$, Z, if it represents an aryl group, includes at least 3 substituents or the quinoline ring is trisubstituted, X represents an ethylene double bond; or a group chosen from —$(CH_2)_n$—, where n is an integer between 1 and 5; —CH($R_d$)—CH($R_e$)—, $R_d$ and $R_e$, identical or different, representing a hydrogen atom, a halogen atom, a hydroxy or epoxy group; —$(CH_2)_{n'}$—O—C(O)—$(CH_2)_m$—, —$(CH_2)_{n'}$—C(O)—O—$(CH_2)_m$—, —$(CH_2)_{n'}$—O—$(CH_2)_m$—, —$(CH_2)_{n'}$—NQ—$(CH_2)_m$—, or —$(CH_2)_{n'}$—S(O)$_t$—$(CH_2)_m$—, where n' is an integer from 0 to 8, m is an integer from 0 to 8, t is zero or an integer equal to 1 or 2, and Q is a hydrogen atom, or an alkyl or aryl radical, as well as the pharmaceutically acceptable salts of these derivatives, their diastereoisomeric forms and their enantiomeric forms.

By "aryl" radical is meant a phenyl or naphthyl radical. "Heterocyclic" designates rings with 5 or 6 elements comprising one, two, three or four heteroatoms, chosen from N, S or O. "Halogen" designates a fluorine, chlorine, bromine atom, or a tritralogeno-methyl group, in particular trichloromethyl. "Alkyl" without further explanation designates a radical with 1 to 5 carbon atoms.

A preferred family of derivatives according to the invention comprises at least one ethylene double bond.

In particular, derivatives in which $R_a$ and/or X represent an ethylenically unsaturated group are concerned.

In a preferred group of this family, X represents an ethylene double bond, and $R_a$ represents a group chosen from —CH=CH—COOH, —CH=CH—COOR, —CH=CH—COH, —CH=CH—COR, —CH=CH—CONH$_2$, —CON($R_x$, $R_y$), and —CH=CH—Z($R_c$).

In another group of this family, X represents a —CH($R_d$)—CH($R_e$)—, or —$(CH_2)_n$— group, and $R_a$ has the meaning given in relation to the above group.

In yet another group, X represents an ethylene double bond and $R_a$ is a radical chosen from —OH, —COOH, or a pharmaceutically acceptable salt, or CN.

Products of this group have the formula II

Formula II

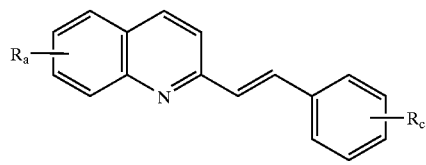

in which $R_a$ represents at least one substituent chosen from an —OH, —COOH group, or a pharmaceutically acceptable salt, or CN, preferably two substituents one of which is an —OH group and the other has one of the above meanings, $R_c$ represents two or three —OH substituents.

In another preferred family of the invention, the quinoline derivatives do not include an ethylene double bond.

A preferred group of this family is constituted by derivatives in which $R_a$ represents a —$(CH_2)_n$—Y group and X is a —CH($R_d$)—CH($R_e$)—, or —$(CH_2)_n$— group.

In another preferred group of this family, X comprises a heteroatom. This concerns in particular products in which X is a group chosen from —$(CH_2)_{n'}$—O—C(O)—$(CH_2)_m$—, —$(CH_2)_{n'}$—$C(O)$—$O$—$(CH_2)_m$—, —$(CH_2)_{n'}$—$O$—$(CH_2)_m$—, —$(CH_2)_{n'}$—$N(Q)$—$(CH_2)_m$—, or —$(CH_2)_{n'}$—$S(O)_t$—$(CH_2)_m$—, where n' is an integer from 0 to 8, m is an integer from 0 to 8, t is zero or an integer equal to 1 or 2, and Q represents a hydrogen atom, an alkyl or aryl radical.

Particularly advantageous products according to the invention include 2-[2-[(3,4-dihydroxyphenyl)ethenyl]]quinoline, 8-hydroxy-2-[2-[(3,4-dihydroxyphenyl)ethenyl]]quinoline, 8-hydroxy-2-[2-[(3,4-dihydroxyphenyl)ethenyl]]7-quinoline carboxylic acid, the sodium salt of 8-hydroxy-2-[2-[(3,4-dihydroxyphenyl)ethenyl]]7-quinolinecarboxylic acid, 7-cyano-8-hydroxy-2-[2-[(3,4-dihydro-xyphenyl)ethenyl]]quinoline, 8-hydroxy-2-[2-[(3.4,5-trihydroxyphenyl)ethenyl]]7-quinoline carboxylic acid, and 2-[2-[(3,4-dihydroxyphenyl)ethenyl]]5,7-quinolinedicarboxylic acid.

The invention also relates to a synthetic process for the derivatives defined above.

This process is characterized in that it comprises
the reaction of a quinaldine of formula III with an aromatic or heteroaromatic derivative of formula IV carrying the appropriate blocking groups:

Formula III

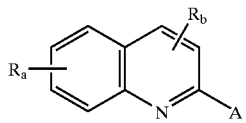

in which A and B represent reactive groups capable of generating group X as defined above, $R_a$, $R_b$, $R_c$ and Z having the meaning given with regard to formula I, but including blocking groups, and
the elimination of the protective groups.

According to an embodiment of the invention, in order to obtain quinoline derivatives in which X does not represent a heteroatom,
a Perkin-type condensation between a quinaldine of formula V and an aromatic or heteroaromatic derivative of formula VI carrying the appropriate blocking groups was used:

Formula V

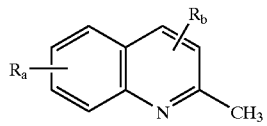

in which the different substituents have the meanings given with regard to formula I, but carrying blocking groups, and
the protective groups are eliminated.

The operation is carried out under reflux in a pyridine-water mixture for approximately 2 hours to 3 days.

In order to prepare for example derivatives corresponding to formula II, a quinaldine of formula V in which $R_a$ represents at least one substituent chosen from the —OH, or —COOH group, or an oxime, and preferably two substituents, one of which is an —OH group, and the other has one of the meanings above, is advantageously reacted with an acetoxybenzaldehyde of formula VII:

Formula VII

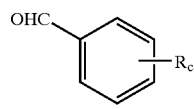

in which $R_c$ represents at least two —OH groups blocked by protective groups.

The condensation stage leads to the formation of quinoline derivatives comprising a double bond represented by X in formula I, and can be treated, if desired, according to standard techniques, to introduce the desired substituents $R_d$ and $R_e$.

The blocking groups are eliminated by hydrolysis.

According to another embodiment of the invention, in order to obtain quinoline derivatives in which X comprises a heteroatom, a quinaldine derivative or formula VIII is used

VIII

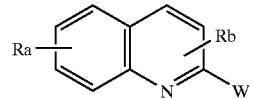

in which W represents —$NH_2$, —$NH(Q)$—OH, —$PO_3H_2$, —Cl, —Br, —$CO_2H$ or —CHO, Q representing a hydrogen atom, an alkyl or aryl radical;
or a quinaldine derivative of formula IX

IX

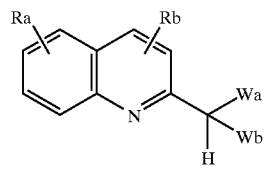

in which Wa represents —Cl, —Br, —$NH_2$, —OH or —$NH(Q)$ where Q represents a hydrogen atom or an alkyl or aryl radical, and Wb represents —H.

More specifically, the following respective reactions were used, with coupling of
a quinaldine derivative of formula VIII in which W=OH, with a derivative of formula X:
$Z(R_c)(CH_2)_n COCl$, according to the diagram

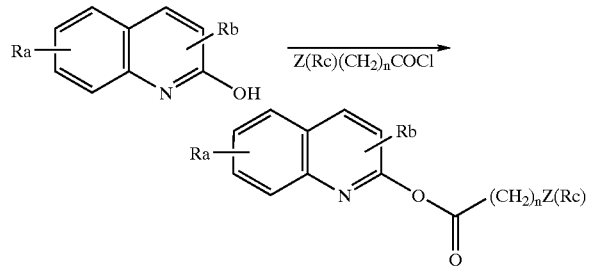

the reaction being avantageously carried out in a pyridine medium,
a quinaldine derivative of formula IX in which the —CH group (Wa, Wb) represents —$CH_2$-$NH_2$, with a derivative of formula XI,
OHC $(CH_2)_n Z(Rc)$, according to the diagram

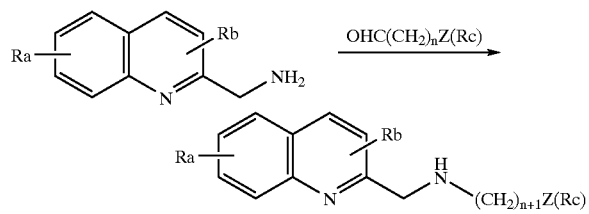

the reaction being avantageously carried out in the presence of $NaBH_3CN$ in an acetic acid medium,
a quinaldine derivative of formula IX in which the —CH group (Wa, Wb) represents a —$CH_2Br$ group, with a derivative of formula XII, $NaS(CH_2)Z(Rc)$, advantageously in the presence of dichloromethane, the coupling being followed by reaction with sodium periodate in order to obtain the corresponding sulphoxide, and, if desired, reacting the sulphoxide with $KHSO_5$ in order to obtain the corresponding sulphone, according to the diagram

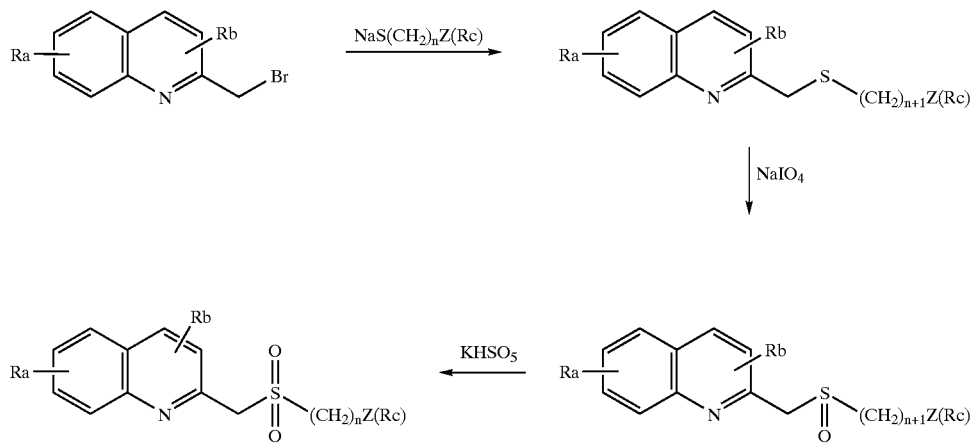

The quinoline derivatives used as starting products in these syntheses are commercially available or easily accessible by synthesis for a person skilled in the art.

Thus, for example, the derivatives of formula VIII in which W represents —NH$_2$ can be obtained by a process comprising:

- condensation of an aromatic amine 1 with an aldehyde 2, by treatment in an acid medium, for example (6N HCl) and heating according to a Doebner-Miller reaction,
- oxidation of quinoline 3 by metachloroperbenzoic acid (mcpba), in a dichloromethane medium, for approximately 14 hours, at ambient temperature, which leads to the N-oxide 4,
- activation of the N-oxide 4 by tosyl chloride (TsCl), in a chloroform medium, at ambient temperature, for approximately 3 hours, followed by treatment with ammonium hydroxide, leading to 2-aminoquinoline 5 being obtained.

This process is illustrated by the following diagram

In order to obtain the derivatives of formula VIII in which W represents Cl, a quinoline 3 is reacted with sodium hypochlorite, which allows a 2-hydroxyquinoline derivative 6 to be obtained, the treatment of which by phosphorous oxychloride produces 2-chloroquinoline 7.

This process is illustrated by the following diagram:

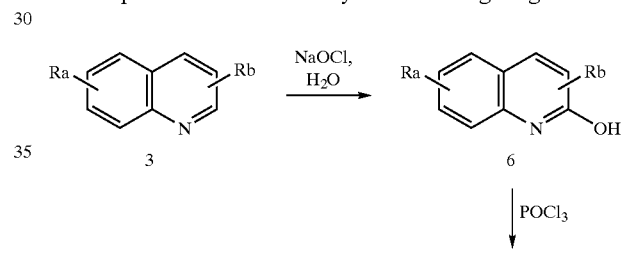

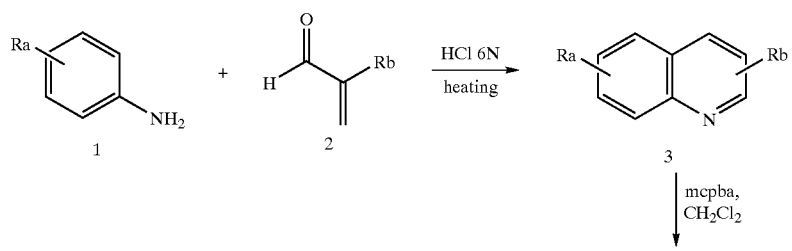

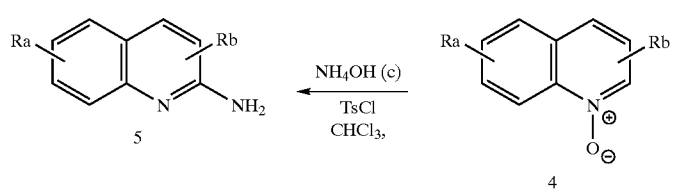

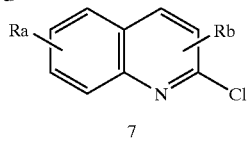

In order to obtain derivatives of formula VIII in which W represents —COOH, a process comprising the following is advantageously used:

condensation of an amine 1 and an aldehyde 8 in an acid medium (for example 6N HCl) and heating, which produces quinaldine 9, oxidation of the methyl by selenium dioxide in order to obtain aldehyde 10, (for example in a dioxane medium and heating), and by enforcing the acid conditions 11. As a variant, the reducing amination of the aldehyde by the cyanoborohydride in an acetic medium produces aminomethylquinoline 12.

This process is illustrated by the following diagram:

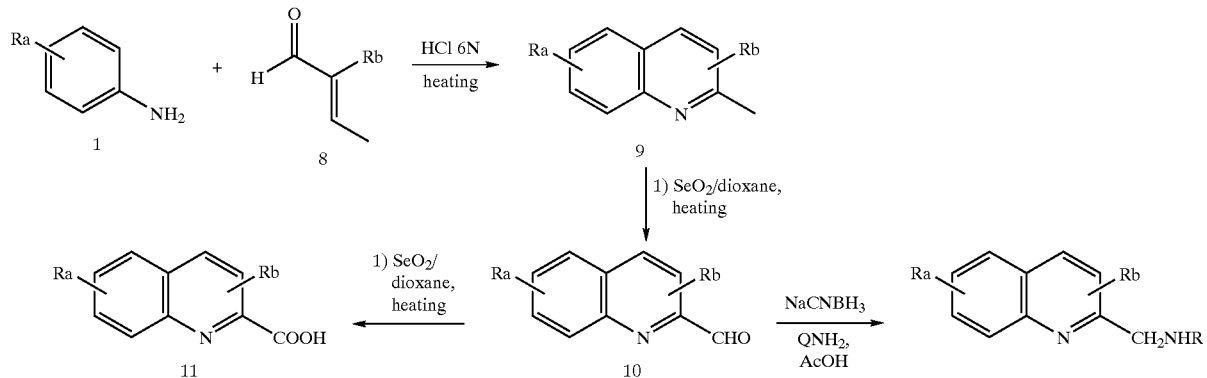

In these formulae, the substituents are defined as indicated above.

In order to obtain quinoline derivatives of formula VIII in which X represents a —CH (Wa, Wb) group with Wa=Br and Wb=H, the bromination of the methyl of quinaldine 9, for example using N-bromosuccinimide, (NBS), which produces compound 13 is advantageously carried out.

This reaction is illustrated by the following diagram:

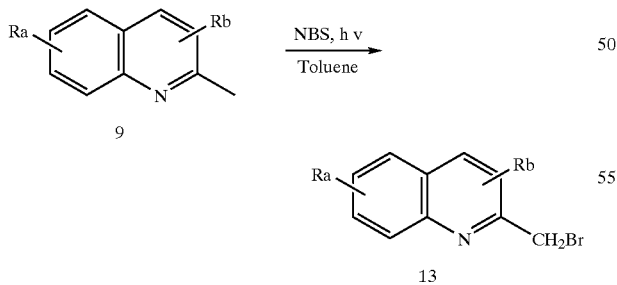

Study of the biological properties of the derivatives of the invention showed an inhibitory activity vis-à-vis HIV integrase and the EcoRI enzyme in vitro. Experiments carried out in vivo have furthermore shown their inhibitory effect on the replication of HIV and the absence of effect on the late phases of the replication of HIV. These results are thus extremely interesting for the treatment of an infection by this virus, especially as the toxicity studies have shown the significant innocuity of these derivatives.

The invention thus relates to pharmaceutical compositions characterized in that they contain an effective quantity of at least one derivative as defined above, in combination with pharmaceutically acceptable vehicles.

These compositions are advantageously used in combination with other anti-HIV medicaments, in particular medicaments endowed with an inhibitory effect vis-à-vis the reverse transcriptase and/or protease.

The doses and administration methods are adapted as a function of the single-drug, two-drug or three-drug combination therapy treatment used.

The invention also relates to the use of the derivatives defined above as biological reagents usable in particular for mechanism studies concerning the viral infection.

Other characteristics and advantages of the a invention are given in the following examples relating to the synthesis of derivatives of formula XII.

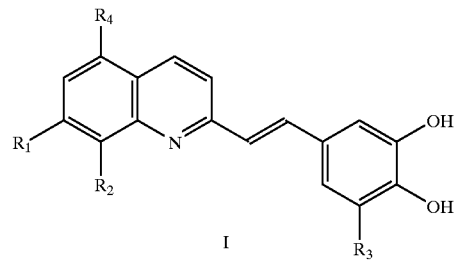

Formula XII and the study of the anti-viral properties of derivatives corresponding to this formula.

SYNTHESIS I OF THE DERIVATIVES OF THE INVENTION

Example 1

2-[2-[(3,4-Dihydroxyphenyl)ethenyl]]quinoline (I, $R_1=R_2=R_3=R_4=H$)

$1^{st}$ stage: preparation of 2-[(3,4-diacetoxyphenyl)ethenyl] quinoline. A mixture of quinaldine (0.90 g, 6.3 mmol) and 3,4-diacetoxybenzaldehyde (1.15 g, 7.0 mmol) in 10 ml of acetic anhydride is taken to reflux for 12 hours. After cooling down to 20° C., the reaction mixture is concentrated under reduced pressure and the residue chromatographied on a silica column eluting with a mixture (cyclohexane/ethyl acetate: 50/50) in order to produce 2.08 g (95%) of 2-[(3,4-diacetoxyphenyl)ethenyl]quinoline which is used without further purification in the following stage.

$2^{nd}$ stage: preparation of 2-[(3,4-dihydroxyphenyl)ethenyl]quinoline. 8 ml of water is added to a solution of the preceding ester (Stage 1) (2.00 g, 5.76 mmol) in pyridine (20 ml). After 3 hours under reflux, the mixture is taken to 20° C., and 20 ml of dichloromethane is added. The phases are separated and the aqueous phase extracted with dichloromethane. The combined organic phases are dried over magnesium sulphate, and concentrated under reduced pressure in order to produce a yellow solid which is recrystallized from isopropanol. (1.51 g, 96%).

M.p. 246–251° C.;

IR (KBr, cm$^{-1}$) n 3536, 1602.

NMR $^1$H (DMSO d6, 200 MHz) d: 6.85 (d, J=8.8 Hz, 1H); 7.10 (dd, J=8.0, 1.0 Hz, 1H) 7.20 (m, 2H); 7.60 (t, J=6.8 Hz, 1H); 7,70–8.10 (m, 5H); 8.35 (d, J=8.8 Hz, 1H); 9.30 (broad s, 2H).

NMR $^{13}$C (DMSO d6, 50 MHz) d: 114.1; 116.0; 119.9 (2C); 125.4; 125.9; 126.9; 127.9 (2C); 128.6; 129.8; 134.8; 136.4; 145.7; 146.9; 147.8; 156.3.

Example 2

8-Hydroxy-2-[2-[(3,4-dihydroxy-phenyl)ethenyl]]quinoline (I, $R_1$=H, $R_2$=OH, $R_3$=H, $R_4$=H)

$1^{st}$ stage: preparation of 8-acetoxy-2-[(3,4-diacetoxyphenyl)ethenyl]quinoline. A mixture of 8-hydroxyquinaldine (2.23 g, 14 mmol) and 3,4-diacetoxybenzaldehyde (2.6 g, 12 mmol) in 30 ml of acetic anhydride is taken to reflux for 12 hours. After cooling down to 20° C., the reaction mixture is concentrated under reduced pressure, taken up in ether and filtered. The solid residue is washed several times with ether in order to produce 3.5 g (61%) of 8-acetoxy-2-[(3,4-diacetoxyphenyl)ethenyl]quinoline which is used without further purification in the following stage.

$2^{nd}$ stage: preparation of 8-hydroxy-2-[(3,4-dihydroxyphenyl)ethenyl]quinoline. 5 ml of water is added to a solution of the preceding ester (Stage 1) (1.40 g, 3.4 mmol) in pyridine (10 ml). After 3 hours under reflux, the mixture is taken to 20° C., and diluted in 30 ml of water. The reaction mixture is then left at 20° C. After 12 hours, the crystals obtained are filtered out, washed with water, with ethanol then with ether. After recrystallisation from xylene, 0.6 g (63%) of yellow crystals are obtained.

M.p. 232–235° C.;

IR (KBr, cm$^{-1}$) n 3410, 1589.

NMR $^1$H (acetone d6, 200 MHz) d: 6.87 (d, J=8.1 Hz, 1H); 7,05–7.10 (m, 2H); 7.21 (d, J=16.2 Hz, 1H); 7.22 (broad s, 1H); 7.72 (d, J=8.7 Hz, 1H); 7,30–7.40 (m, 2H); 7.91 (d, J=16.2 Hz, 1H); 8.23 (d, J=8.7 Hz, 1H), 8,20–8.70 (massive, 3H).

NMR $^{13}$C (DMSO d6, 50 MHz) d: 111.2; 114.0; 116.0; 117.7; 119.2; 120.8; 124.7; 126.7; 127.5; 128.2; 135.1; 136.4; 138.2; 145.7; 146.8; 152.9; 154.1.

Example 3

8-Hydroxy-2-[2-[(3,4-dihydroxyphenyl)ethenyl]]7-quinoline Carboxylic Acid (I, $R_1$=CO$_2$H, $R_2$=OH, $R_3$=H, $R_4$=H)

A mixture of 8-hydroxy-7-quinaldine carboxylic acid (1.20 g, 6 mmol) and 3,4-diacetoxybenzaldehyde (1.8 g, 8 mmol) in 15 ml of acetic anhydride is taken to reflux for 12 hours.

The 8-hydroxy-7-quinaldine carboxylic acid is synthethized by operating according to Meek et al in J. Chem. Engineering data, 1969, 14, 388–391.

After cooling down to 20° C., the reaction mixture is concentrated under pressure. The residue obtained is dissolved in pyridine (20 ml), 8 ml of water is added. After 3 hours under reflux, the mixture is taken to 20° C. and diluted with 20 ml of water. The mixture is extracted with dichloromethane, the organic phase is removed and the aqueous phase is left at 20° C. After 12 hours, the crystals obtained are filtered out, washed with water, with ethanol then with ether, then dried under vacuum in order to produce 0.96 g (50%) of bright red crystals.

M.p.≧300° C.;

IR (KBr, cm$^{-1}$) n 3091, 1667, 1589.

NMR $^1$H (DMSO d6, 200 MHz) d: 6.80 (d, J=8.1 Hz, 1H); 7.04 (dd, J=8.2; 1.5 Hz, 1H); 7,10–7.18 (m, 2H); 7.45 (d, J=16.2 Hz, 1H); 7,78–7.90 (m, 2H), 8.15 (d, J=8.8 Hz, 1H); 8.48 (d, J=8.8 Hz, 1H); 9.22 (s, broad, 1H); 9.52 (s, broad, 1H).

NMR $^{13}$C (DMSO d6, 50 MHz) d: 112.8; 113.2; 114.2, 116.0; 120.2; 120.7; 120.9; 127.3; 127.5; 130.5; 135.2; 139.2; 140.0; 145.7; 148.0; 152.8; 160.8; 170.6.

Example 4

Sodium Salt of 8-Hydroxy-2-[2-[(3,4-dihydroxyphenyl)ethenyl]]7-quinolinecarboxylic Acid (I, $R_1$=CO$_2$Na, $R_2$=OH, $R_3$=H, $R_4$=H)

The acid (I, $R_1$=CO$_2$H, $R_2$=OH, $R_3$=H) (0.1 g, 0.3 mmol) is added in portions to a solution of 0.1 M soda maintained under a nitrogen atmosphere. The mixture is then lyophylized (−40 to +40° C.) in order to produce 0.11 g of the sodium salt (quantitative) in the form of a grey-brown solid.

IR (KBr, cm$^{-1}$) n 3436, 1598, 1561.

NMR $^1$H (DMSO d6, 200 MHz) d: 4,5–5.5 (massif, 2H); 6.74 (d, J=7.8 Hz, 1H); 6.95 (m, 2H); 7.13 (s, 1H); 7.24 (d, J=16.4 Hz, 1H); 7.49 (d, J=16.4 Hz, 1H); 7.75 (d, J=8.4 Hz, 1H); 7.84 (d, J=8.6 Hz, 1H); 8.08 (d, J=8.6 Hz, 1H); 12.6 (broad s, 1H).

NMR $^{13}$C (DMSO d6, 50 MHz) d: 111.9; 113.7; 114.9; 115.8; 119.2; 119.5; 126.0; 127.0; 127.5; 129.9; 133.6; 136.0; 141.1; 146.2; 147.7; 154.0; 163.7; 171.6.

Example 5

7-Cyano-8-hydroxy-2-[2-[(3,4-dihydroxyphenyl)ethenyl]]quinoline (I, $R_1$=CN, $R_2$=OH, $R_3$=H, $R_4$=H)

$1^{st}$ stage: preparation of 8-hydroxy-7-quinaldine carbaldehyde oxime.

0.73 g (10 mmol) of hydroxylamine hydrochloride then 0.87 g (0.01 mmol) of sodium acetate are added successively to a solution of 8-hydroxy-7-quinaldine carbaldehyde (1 g, 53 mmol) in acetic acid (20 ml). The 8-hydroxy-7-quinaldine carbaldehyde is synthethised by operating according to Przystal et al, J. Heterocycl. Chem, 1967, 4, 131–2.

The mixture is heated at 100° C. for 1 hour then concentrated under reduced pressure. The residue is taken up in 20 ml of water and extracted with dichloromethane. The organic phases are combined, dried over MgSO$_4$ and con centrated in order to produce 0.7 g of the expected oxime in the form of a yellow solid (65%).

M.p.=171–175° C.

IR (KBr, cm$^{-1}$) n 3200–2800, 1643, 1614, 1563.

Analysis of the NMR spectrum shows the presence of two syn/anti isomers, only the majority isomer is described below.

NMR $^1$H (DMSO d6, 200 MHz) d: 2.68 (s, 3H); 7.32 (d, J=8.6 Hz, 1H); 7.42 (d, J=8.3 Hz, 1H); 7.70 (d, J=8.6 Hz, 1H); 8.16 (d, J=8.4 Hz, 1H); 8.50 (s, 1H)

NMR $^{13}$C (DMSO d6, 50 MHz) d: 24.7; 115.2, 117.9; 122.9; 123.2; 127.2; 136.2; 138.1; 144.7, 150.8; 157.4.

2$^{nd}$ stage: preparation of 7-cyano-8-acetoxy-2-[(3,4-diacetoxyphenyl)ethenyl]quinoline. A mixture of 8-hydroxy-7-quinaldine carbaldehyde oxime (0.60 g, 2.9 mmol) and 3,4-diacetoxybenzaldehyde (0.78 g, 3.4 mmol) in 10 ml of acetic anhydride is taken to reflux for 12 hours. After cooling down to 20° C., the reaction mixture is concentrated under reduced pressure. The residue obtained is chromatographied on a silica column eluting with a mixture (cyclohexane/ethyl acetate: 50/50) in order to produce 0.77 g (62%) of light yellow solid.

IR (KBr, cm$^{-1}$) n 2941, 2223, 1782, 1600, 1504.

NMR $^1$H (CDCl$_3$, 200 MHz) d: 2.30 (s, 3H); 2.31 (s, 3H); 2.60 (s, 3H); 7,00–7.70 (m, 8H); 8.09 (d, J=8.6 Hz, 1H).

NMR $^{13}$C (CDCl$_3$, 50 MHz) d: 20.7 (2C); 20.8; 106.8; 115.3; 122.0; 122.6; 123.8; 125.7; 126.2; 129.0; 130.7; 134.3; 134.9; 136.4; 140.5; 142.4; 142.5; 151.6; 156.8; 168.1 (2C); 68.5.

3$^{rd}$ stage: preparation of 7-cyano-8-hydroxy-2-[(3,4-dihydroxyphenyl)ethenyl]quinoline. 5 ml of water is added to a solution of the preceding triester (Stage 2) (0.60 g, 1.4 mmol) in pyridine (10 ml). After 3 hours under reflux, the mixture is taken to 20° C. and diluted with 20 ml of water. The phases are separated and the aqueous phase extracted with dichloromethane. The combined organic phases are dried over sulphate magnesium, and concentrated under reduced pressure in order to produce a yellow solid which is recrystallized from isopropanol (0.3 g, 71%).

M.p. 239–244° C.

IR (KBr, cm$^{-1}$) n 3411, 2194, 1603, 1554.

NMR $^1$H (DMSO d6, 200 MHz) d: 6.79 (d, J=8.2 Hz, 1H); 7.00 (d, J=8.4 Hz, 1H); 7,05–7.25 (m, 2H); 7.41 (d, J=8.5 Hz, 1H); 7.54 (d, J=8.5 Hz, 1H); 7.87 (d, J=8.6 Hz, 1H); 8.04 (d, J=16.2 Hz, 1H); 8.32 (d, J=8.6 Hz, 1H); 8,80–9.50 (massive, 3H).

NMR $^{13}$C (DMSO d6, 50 MHz) d: 114.0; 115.9; 117.1; 118.5; 119.9; 123.3; 123.7; 123.9; 126.5; 127.8; 129.6; 136.7; 137.6; 145.6; 147.0; 149.6; 155.7; 158.2.

Example 6

8-Hydroxy-2-[2-[(3,4,5-trihydroxyphenyl)ethenyl]] 7-quinoline Carboxylic Acid (I, R$_1$=CO$_2$H, R$_2$=R$_3$= OH, R$_4$=H)

A mixture of 8-hydroxyquinaldine carboxylic acid (0.23 g, 1.13 mmol) and 3,4,5-triacetoxybenzaldehyde (0.32 g, 1.16 mmol) in 7 ml of acetic anhydride is taken to reflux for 48 hours. After cooling down to 20° C., the reaction mixture is concentrated under reduced pressure. The residue obtained is dissolved in pyridine (7 ml), 3 ml of water is added. After 3 hours under reflux, the mixture is taken to 20° C. and diluted with 20 ml of water. The mixture is extracted with dichloromethane, the organic phase is removed and the aqueous phase is left at 20° C. After 12 hours, the crystals obtained are filtered, washed in water, with ethanol then with ether, then dried under vacuum in order to produce 0.15 g (40%) of bright red crystals.

M.p.≧300° C.;

IR (KBr, cm$^{-1}$) n 3600–2400, 1630, 1585.

NMR $^1$H (DMSO d6, 200 MHz) d: 3,50–5.50 (massive, 4H); 6.68 (s, 2H); 7.16 (d, J=8.4 Hz, 1H); 7.44 (d, J=16.1 Hz, 1H); 7.80 (d, J=16.1 Hz, 1H); 7.84 (d, J=8.4 Hz, 1H); 8.21 (d, J=8.8 Hz, 1H); 8.51 (d, J=8.8 Hz, 1H); 9.19 (s, broad, 1H).

NMR $^{13}$C (DMSO d6, 50 MHz) d: 107.4 (2C); 112.9; 113.2; 120.0; 120.8; 126.2; 127.8; 130.5; 134.9; 136.3; 140.1; 140.4; 146.4 (2C); 152.7; 161.0; 170.6.

Example 7

2-[2-[(3.4,-Dihydroxyphenyl)ethenyl]]5,7-quinolinedicarboxylic Acid (R$_1$=R$_4$=CO$_2$H, R$_2$=R$_3$= H)

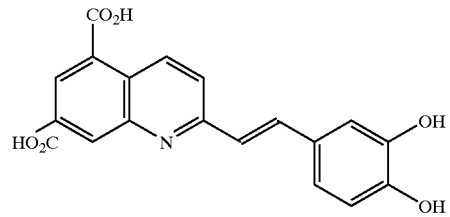

1$^{st}$ stage: preparation of 2-methyl-5,7-quinolinedicarboxylic acid: A solution of 5-amino-1,3-benzenedicarboxylic acid (5.3 g, 29 mmol) in 60 ml of 6N hydrochloric acid is taken to reflux. 2.6 ml (32 mmol) of crotonaldehyde is added dropwise over a period of one hour and heating is maintained for one hour. After cooling down to 20° C., the mixture is extracted with ether. The organic phase is removed and the aqueous phase is basified with a 30% solution of ammonium hydroxide. The precipitate is filtered, washed with water then with ether and dried under vacuum to produce 2.5 g of 2-methyl-5,7-quinolinedicarboxylic acid (Yield: 37%).

NMR $^1$H (CD$_3$OD, 200 MHz) δ: 1.30 (s, 3H); 6.40 (d, J=8.8 Hz, 1H); 7.20 (s,2H) 8.25 (d, J=8.8 Hz, 1H).

2$^{nd}$ stage: preparation of 2-[2-[(3,4-dihydroxyphenyl)ethenyl]]5,7-quinolinedicarboxylic acid: A mixture of 2-methyl-5,7-quinolinedicarboxylic acid (0.60 g, 2.6 mmol) and 3,4-diacetoxybenzaldehyde.

(0.71 g, 3.1 mmol) in 10 ml of acetic anhydride is taken to reflux for 48 hours. After cooling down to 20° C., the reaction mixture is concentrated under reduced pressure and the residue is taken up in pyridine (10 ml). The mixture is taken to reflux, then 3 ml of water are added. After 3 hours under reflux, the mixture is taken to 20° C., and 25 ml of an aqueous solution of acetic acid is added. The mixture is extracted with dichloromethane. The organic phases are combined, dried over magnesium sulphate and concentrated under reduced pressure in order to produce a red solid which is recrystallized from isopropanol.

NMR $^1$H (DMSO d6, 200 MHz) δ: 6.78 (d, J=8.2 Hz, 1H); 7,00–7.30 (m, 3H); 7.74 (d, J=16.2 Hz, 1H); 8.03 (d, J=9.2 Hz, 1H); 8.56 (s, 1H); 8.64 (s, 1H); 9.22 (d, J=9.2 Hz, 1H).

II STUDY OF ANTI-VIRAL PROPERTIES DIRECTED AGAINST DERIVATIVES OF HIV-1 INTEGRASE ACCORDING TO THE INVENTION

The anti-integrase and antiviral activities of the following compounds are described hereafter by way of example:

Compound 1: 8-hydroxy-2-[2-[(3,4-dihydroxyphenyl)ethenyl]]7-quinoline carboxylic acid ($R_1=CO_2H$, $R_2=OH$, $R_3=R_4=H$)

Compound 2: sodium salt of 8-hydroxy-2-[2-[(3,4-dihydroxyphenyl)ethenyl]]7-quinoline-carboxylic acid ($R_1=CO_2Na$, $R_2=OH$, $R_3=R_4=H$)

Compound 3: 8-hydroxy-2-[2-[(3,4,5-trihydroxyphenyl)ethenyl]]7-quinoline carboxylic acid ($R_1=CO_2H$, $R_2=R_3=OH$, $R_4=H$)

Compound 7: 2-[2-[(3,4-dihydroxyphenyl)ethenyl]]5,7-quinolinecarboxylic acid ($R_1=R_4=COOH$; $R_2=R_3=H$)

EXAMPLE 1

Inhibition of the in vitro Activity of HIV-1 Integrase

The activity of HIV-1 integrase is measured by the three following tests:

1—The endonucleolytic activity of the protein is tested on a double-strand oligonucleotide of 21 base pairs, radiolabelled at the 5' end. The activity of the integrase is expressed by elimination of the dinucleotide at the 3' end.

2—The strand transfer test is carried out with a double-strand oligonucleotide of 21 base pairs mimicking the end of the viral DNA, the 3' terminal dinucleotide of which has been supressed. The activity of the protein is expressed by the covalent insertion of this oligonucleotide in a homologous oligonucleotide.

3—The disintegration test is carried out with a substrate mimicking the structure of the integrated viral DNA. The quantity of DNA excised by the integrase is measured. This last test only quantifies the catalytic activity of the protein excluding its fixation activity on the DNA.

Compounds 1 and 3, according to the present invention, inhibit the three activites of HIV-1 integrase. The disintegration inhibition suggests that these are inhibitors of the catalytic activity of the enzyme. The inhibition levels in the three tests for each of the compounds are comparable, which shows that compounds 1 and 3 do not interfere with the fixation of the integrase on its substrate. Table I shows the inhibitory activities of the compounds according to the invention. The inhibition is expressed as the concentration necessary to block 50% of the activity of HIV-1 integrase.

TABLE I

Inhibition of the in vitro activity of HIV-1 integrase by compounds 1 and 3 according to the present invention

| | endonucleolytic cleavage | strand transfer | disintegration |
|---|---|---|---|
| Compound 1 | 0.9 µM | 0.9 µM | 0.5 µM |
| Compound 3 | 0.32 µM | 0.31 µM | 0.056 µM |

Note:
Compound 2 which is the sodium salt of free acid 1 has the same anti-integrase activity as that in the tests for in vitro activity. Compound 2 is soluble in the water at 10 mM whilst compound 1 is soluble in DMSO.

EXAMPLE 2

Inhibition of the EcoRI Restriction Enzyme

The catalytic site of HIV-1 integrase is very close to that of the EcoRI restriction enzyme. The compounds which block both proteins are therefore catalytic inhibitors of integrase.

Compound 1 according to the present invention inhibits the cleavage of a linearized plasmid by the EcoRI enzyme. The test is carried out in the following manner: The pSP65 plasmide is linearized and radiolabelled at its 5' end by the kinase polynucleotide. The linearized plasmid is incubated for 4 hours in the presence of 0.1 units of the EcoRI enzyme. The enzyme activity is monitored by the appearance of the cleavage products on 1.2% agarose gel.

In the presence of compound 1 according to the present invention, cleavage by EcoRI is strongly inhibited. This compound is therefore an inhibitor of the catalytic activity of the protein.

EXAMPLE 3

Absence of Reverse Transcription Inhibition by Compound 1

The specificity of the compounds according to the invention for integrase is estimated by an activity test on the reverse transcriptase enzyme of the HIV-1 virus. This test is carried out in the following manner: The viral particles of a supernatant of a CEM cell culture (established lymphocyte line) are concentrated by centrifugation at 30,000 RPM. These viral particles are lysed in a non-ionic detergent and their reverse transcriptase activity is tested on a substrate formed from a hybridized oligo (dG) primer on a polyrC matrix. In the presence of radiolabelled nucleotide dG, the transcriptase activity is expressed by the formation of labelled polynucleotide which can be precipitated in trichloroacetic acid. This confirms that a dideoxynucleotide ddG inhibits the formation of acid precipitatable.

In the presence of compound 1, no reverse transcription inhibition of a polyrc matrix is observed. This result shows the good selectivity of compound 1 for viral integrase.

EXAMPLE 4

Inhibition of the Replication of the Human Immunodeficiency Virus (HIV-1)

The activity test consists of putting the cells of an established lymphocyte line, CEM cells, in contact with a supernatant of infected cells containing the infectious virions. The test is carried out in the following manner: The CEM cells, cultured in suspension in RPMI medium supplemented with 10% of foetal calf serum, are infected with a viral supernatant with a multiplicity of infection of 0.5. After 2 hours of infection, the cells are washed twice with RPMI medium in a manner so as to eliminate the residual viral particles. Finally, the cells are replaced in RPMI medium containing the compound according to the invention. The viral load is evaluated after 72 hours of culture. This is quantified in two of the following ways:

1) The quantity of viral protein p24 is determined by an ELISA test. 2) The infectious virus load is estimated by infecting Hela β-gal $CD4^+$ cells (cf. paragraph 4).

The toxicity of the compounds is tested by a biotransformation test of MTT to formazan by cellular mitochondrial dehydrogenases.

In the two activity tests, compound 1 according to the present invention has a protective effect against the infection of the CEM cells by HIV-1. This protective effect is expressed by the inhibition of the production of viral par ticles with an 50% effectiveness of 4 μM according to the HeLaβ-gal test and with a 50% effectiveness of 28 μM according to the p24 test. Compound 1 is devoid of toxicity at 100 μM, maximum concentration tested, on CEM cells after the MTT test.

Compound 2 blocks the production of viral particles, measured by the ELISA p24 test, during the infection with CEM cells. This compound is also devoid of toxicity up to 100 μM according to the MTT test.

These results are summarized in Table II.

Compound 2 which corresponds to the sodium salt of free acid 1 has the same anti-viral effect measured by the inhibition of replication in CEM cells after 72 hours.

EXAMPLE 5

Absence of Inhibition in the Late Stages of the Replication of HIV-1 by Compound 1

The compounds according to the present invention were tested on the late stages of the replication of HIV-1. The test is as follows: The ACH2 cells which integrated HIV-1 viral DNA were used. These cells do not express the viral proteins and do not therefore produce the virus unless activated by TNF. When the cells are used in the presence of TNF, they express the HIV virus from the integrated provirus. The production of viral particles is detected 24 hours after activation. The viral load in the supernatant is quantified by the ELISA p24 test.

No other significant effect was detected on the production of viral particles after 24 hours when the ACH2 cells are treated with concentrations of compound 1 up to 100 μM. A slight inhibition is observed above 50 μM but the inhibitory 50% concentration is not achieved at 100 μM.

TABLE II

| | Anti-viral effect of compound 1 | | |
|---|---|---|---|
| | MTT[i] | β-gal[j] activity | p24[k] test |
| CEM[a] cell | >100 μM | 4 μM | 20 μM |
| ACH2[b] cells | >100 μM | — | >100 μM |

TABLE III

| | Anti-viral effect of compound 1 | | |
|---|---|---|---|
| | MTT[i] | β-gal[j] activity | p24[k] test |
| CEM[a] cell | >100 μM | 1 μM | 4 μM |
| ACH2[b] cells | >100 μM | — | >100 μM |

[a]global antiviral effect;
[b]effect on the late stages
[i]Toxicity by biotransformation;
[j]colorimetric test;
[k]ELISA test In conclusion, the compounds given by way of example selectively inhibit the in vitro activity of HIV-1 integrase in the three tests used. Compound 1, which is devoid of cytotoxicity up to 100 μM in the cellular models used, block the replication of HIV by interfering with an early stage of the replication cycle. Given the absence of effect on in vitro reverse transcription, this stage is probably the integration of the viral genome in the genome of the infected cell.

What is claimed is:

1. A quinoline compound or its salt, according to general formula I

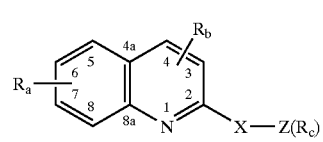

Formula I in which $R_a$, $R_b$ and $R_c$, identical or different from one another, represent one or more substituents, themselves identical or different, occupying any position on the rings, the substituents being chosen from a —$(CH_2)_n$—Y or —CH=CH—Y group, where Y represents a halogen atom, an —OH, —OR, —COH, —COR, —COOH, —COOR, —COH, —COR, —$CONH_2$, —$CON(R_x, R_y)$, —CH=NOH, —CO—CH=NOH, —$NH_2$, —$N(R_x, R_y)$, —$NO_2$, —$PO(OR)_2$, —$SH_2$, —SR, —$SO_2R$, —$SO_2NHR$, —CN, or $Z(R_c)$ radical, where R represents an alkyl radical with 1 to 8 carbon atoms, or an aryl or heterocyclic radical, $R_x$ and $R_y$, identical or different, represent an alkyl radical with 1 to 5 carbon atoms, Z represents an aryl or heterocyclic radical and n is zero or an integer from 1 to 5, $R_b$ moreover can represent a hydrogen atom, and when Y represents a —COOH or —COOR group in $R_c$, Z, if it represents an aryl group, includes at least 3 substituents or the quinoline ring is trisubstituted, X represents an ethylene double bond, or a —$(CH_2)_n$— group, where n is an integer from 1 to 5, or a —CH $(R_d)$—CH$(R_e)$— group, $R_d$ and $R_e$, identical or different, representing a hydrogen atom, halogen atom, a hydroxy or epoxy group, or a —$(CH_2)_{n'}$—O—C (O)—$(CH_2)_m$—, —$(CH_2)_{n'}$—C(O)—O—$(CH_2)_m$—, —$(CH_2)_{n'}$—O—$(CH_2)_m$—, —$(CH_2)_{n'}$—N(Q) —$(CH_2)_m$— or —$(CH_2)_{n'}$—S(O)$_t$—$(CH_2)_m$— group, where n' is an integer from 0 to 8, m is an integer from 0 to 8, t is zero or an integer equal to 1 or 2, and Q represents a hydrogen atom, an alkyl or aryl radical, as well as the pharmaceutically acceptable salts of these derivatives, their diastereoisomeric forms and their enantiomeric forms.

2. A compound or its salt according to claim 1, wherein there is at least one ethylene double bond and wherein at least one of $R_a$ and X represents an ethylenically unsaturated group.

3. A compound or its salt according to claim 2, in which X represents an ethylene double bond, or a —CH($R_d$)—CH $(R_e)$—, or —$(CH_2)_n$— group and $R_a$ is a group chosen from —CH=CH—COOH, —CH=CH—COOR, —CH=CH —COH, —CH=CH—COR, —CH=CH—$CONH_2$, —$CON(R_x, R_y)$, and —CH=CH—$Z(R_c)$.

4. A compound or its salt according to claim 2, wherein X represents an ethylene double bond and $R_a$ is a radical chosen from —OH, —COOH, or a pharmaceutically acceptable salt, or CN, wherein said compound or salt corresponds to formula II

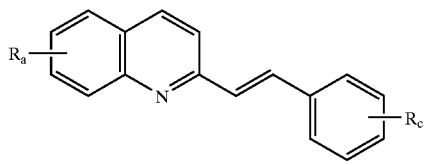

Formula II in which

R<sub>a</sub> represents at least one substituent chosen from an —OH, —COOH group, or a pharmaceutically acceptable salt, or CN, preferably two substituents, one of which is an —OH group, and R<sub>c</sub> represents two or three —OH substituents.

5. A compound or its salt according to claim 1, wherein said compound or salt does not comprise an ethylene double bond and wherein $R_a$ represents a —(CH$_2$)$_n$—Y group and X is a —CH(R$_d$)—CH(R$_e$)— or —(CH$_2$)$_n$— group, or comprises a heteroatom and correspond to one of the —(CH$_2$)$_{n'}$—O—C(O)—(CH$_2$)$_m$—, —(CH$_2$)$_{n'}$—C(O)—O—(CH$_2$)$_m$—, —(CH$_2$)$_{n'}$—, —O—(CH$_2$)$_m$—, —(CH$_2$)$_{n'}$—N(Q)—(CH$_2$)$_m$—, or —(CH$_2$)$_{n'}$—S(O)$_t$—(CH$_2$)$_m$— groups.

6. A quinoline compound or its salt according to claim 1, selected from the group consisting of 2-[2-[(3,4-dihydroxyphenyl)ethenyl]]quinoline, 8-hydroxy-2-[2-[(3,4-dihydroxyphenyl)ethenyl]]quinoline, 8-hydroxy-2-[2-[(3,4-dihydroxyphenyl)ethenyl]]7-quinoline carboxylic acid, the sodium salt of 8-hydroxy-2-[2-[(3,4-dihydroxyphenyl)ethenyl]]7-quinoline carboxylic acid, 7-cyano-8-hydroxy-2-[2-[(3,4dihydroxyphenyl)ethenyl]]quinoline, 8-hydroxy-2-[2-[(3,4,5-trihydro-xyphenyl)ethenyl]]7-quinoline carboxylic acid, and 2-[2-[(3,4-dihydroxyphenyl)ethenyl]]5,7-quinolinedicarboxylic acid.

7. Synthetic process for the preparation of a compound or its salt according to claim 1, comprising reacting a quinaldine of formula III with an aromatic or heteroaromatic derivative of formula IV carrying the appropriate blocking groups:

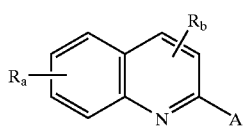

Formula III in which A and B represent reactive groups capable of generating group X as defined above, R<sub>a</sub>, R<sub>b</sub>, R<sub>c</sub> and Z having the meanings given with regard to formula I, but include blocking groups, and eliminating the blocking groups.

8. Process according to claim 7, for preparation of a compound or salt of formula I in which X does not represent a heteroatom, comprising reacting a quinaldine of formula V and an aromatic or heteroaromatic derivative of formula VI carrying the appropriate blocking groups,

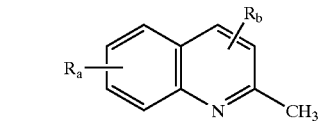

Formula V

OHC—Z(R<sub>C</sub>)    Formula VI wherein the substituents have the meanings given with regard to formula I but include blocking groups, and eliminating the blocking groups.

9. Synthetic process for preparing a compound or salt of formula II according to claim 4, comprising reacting a quinaldine of formula V in which R<sub>a</sub> represents at least one substituent chosen from the —OH, —COOH group, or an oxime, and preferably two substituents, one of which is an —OH group, and the other has one of the above meanings, with an acetoxybenzaldehyde of formula VII:

Formula VII

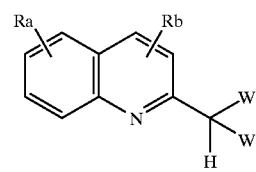

in which R<sub>c</sub> represents at least two —OH groups blocked by protective groups.

10. Process according to claim 7, for preparation of a compound or salt in which X comprises a heteroatom, wherein the quinaldine compound is a compound corresponding to formula VIII Formula VIII

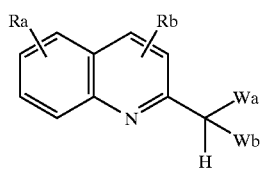

in which W represents —NH<sub>2</sub>, —NH(Q), —OH, —PO<sub>3</sub>H<sub>2</sub>, —Cl, Br, —CO<sub>2</sub>H, or —CHO, and Q represents a hydrogen atom, an alkyl or aryl radical, or a quinaldine compound corresponding to formula IX Formula IX in which Wa represents —Cl, —Br, —NH<sub>2</sub>, —OH or —NH(Q) where Q represents a hydrogen atom or an alkyl or aryl radical, and Wb represents —H.

11. Process according to claim 10, comprising coupling a quinaldine compound of formula VIII in which W is OH, with a compound of formula X:

Z(R<sub>c</sub>)(CH<sub>2</sub>)<sub>n</sub>COCl, or a quinaldine compound of formula IX in which the —CH(Wa, Wb) group represents —CH<sub>2</sub>—NH<sub>2</sub>, with a compound of formula XI, OHC(CH<sub>2</sub>)<sub>n</sub>Z(R<sub>c</sub>), or a quinaldine compound of formula IX in which the —CH (Wa, Wb) group represents a —CH$_2$Br group, with a compound of formula XII, NaS(CH$_2$)$_n$Z(R$_c$), this coupling being followed by reaction with sodium periodate in order to obtain the corresponding sulphoxide and, if desired, reaction of the sulphoxide with KHSO$_5$ in order to obtain the corresponding sulphone.

12. A pharmaceutical composition comprising a therapeutically effective amount of at least one compound or its salt as defined in claim 1, in combination with a pharmaceutically acceptable vehicle.

* * * * *